(12) United States Patent
Matsushima

(10) Patent No.: US 7,202,393 B2
(45) Date of Patent: Apr. 10, 2007

(54) MOUSE MODEL FOR TYPE II DIABETES

(76) Inventor: Yoshibumi Matsushima, B-5, Higashi-Omiya-Kosha, 3-7-4, Higashi-Omiya, Minuma-Ku, Saitama-Shi, Saitama-Ken (JP)

( * ) Notice: Subject to any disclaimer, the term of this patent is extended or adjusted under 35 U.S.C. 154(b) by 0 days.

(21) Appl. No.: 11/041,013

(22) Filed: Jan. 21, 2005

(65) Prior Publication Data

US 2006/0021072 A1    Jan. 26, 2006

(30) Foreign Application Priority Data

Jul. 23, 2004   (JP) .............................. 2004-215927

(51) Int. Cl.
*A01K 67/00* (2006.01)
*A01K 67/033* (2006.01)
*A01K 67/027* (2006.01)
*C12N 15/00* (2006.01)

(52) U.S. Cl. .............................. 800/9; 800/18; 800/21
(58) Field of Classification Search .................... 800/9, 800/18, 21
See application file for complete search history.

(56) References Cited

FOREIGN PATENT DOCUMENTS

JP          20040651581          3/2004

OTHER PUBLICATIONS

Ueda et al., 1999, Diabetes, 48: 1168-1174.*
Alberts, et al., 1994, Molecular Biology of the Cell, 3rd ed. Garland Publishing, Inc., New York, pp. 1016-1017.*
Ueda et al., 1995, Diabetologia, 38: 503-508.*
Yoshioka et al., "A Novel Locus, *Mody4*, Distal to D7Mit189 on Chromosome 7 Determines Early-Onset NIDDM in Nonobese C57BL/6 (Akita) Mutant Mice", Diabetes, May 1997, pp. 887-894, vol. 46.
Ueda et al., "The NSY Mouse: A New Animal Model of Spontaneous NIDDM with Moderate Obesity", Diabetologia, 1995, pp. 503-508, vol. 38.
Hattori et al., "The NOD Mouse: Recessive Diabetogenic Gene in the Major Histocompatibility Complex" et al., Science, Feb. 1986, pp. 733-742, vol. 231.
Herberg et al., "Adrenal Function and the Effect of a High-Fat Diet on C57BL/6J and C57BL/6J-ob/ob Mice", Horm. Metab. Res., 1975, pp. 410-415, vol. 7.
Nishimura, "Breeding of Mice Strains for Diabetes Mellitus", Exp. Animals, 1969, pp. 147-157, vol. 18.
Hummel et al., "Diabetes, a New Mutation in the Mouse", Science, Sep. 1966, pp. 1127-1128, vol. 153.

* cited by examiner

*Primary Examiner*—Anne M. Wehbe'
*Assistant Examiner*—Joanne Hama
(74) *Attorney, Agent, or Firm*—The Webb Law Firm

(57) ABSTRACT

The present invention relates to a Type II diabetes model mouse, having a causative gene responsible for the following characteristics (1) to (3) in the heterologous or homologous state, wherein the characteristics are autosomal recessive genetic traits: (1) having a higher blood sugar level as compared to a normal strain mouse at 10 to 14 weeks of age and having a blood glycosylated hemoglobin concentration of 2.5% or higher at 10 to 14 weeks of age or older; (2) being positive in test for urine sugar at 10 to 14 weeks of age; and (3) exhibiting essentially no inflammation of the pancreatic islets and having a blood insulin concentration equivalent to or higher than that of a normal strain mouse. According to the present invention, there is provided a novel mouse having a gene responsible for the spontaneous development of type II diabetes.

6 Claims, 1 Drawing Sheet

MOUSE MODEL FOR TYPE II DIABETES

CROSS-REFERENCE TO RELATED APPLICATION

This application is based on and claims the benefit of priority from the prior Japanese Patent Application No. 2004-215927, filed on Jul. 23, 2004, the entire contents of which are incorporated herein by reference.

BACKGROUND OF THE INVENTION

1. Field of the Invention

The present invention relates to mice having a gene responsible for the spontaneous development of Type II diabetes.

2. Background Technology

Diabetes, in particular Type II diabetes (insulin-independent diabetes mellitus) has long been known as a lifestyle-related disease and is one of the diseases with a rapidly increasing number of patients worldwide. Although a drastic change in lifestyle is pointed out as a primary reason for such a rapid increase in the number of patients, a genetic factor is also significantly involved. The rapid increase in the number of patients presses the urgency for the development of an appropriate method for the prevention and treatment of diabetes, the elucidation of a causative gene and the clarification of the onset mechanism. For this purpose, an appropriate disease model animal is indispensably needed. In particular, a spontaneous disease model animal is useful in elucidating a causative gene and the like.

Examples of conventionally reported model animals which spontaneously develop Type II diabetes include KK-Ay mice (Nishimura M., Exp. Anim. 18, 147–157, 1969), NSY mice (Ueda H., et al., Diabetologia 38, 503–508, 1995), db/db mice (Hummel K. P., et al., Science 153, 1127–1128, 1966), ob/ob mice (Herberg L. & Kley H K, Horm. Metab. Res. 7, 410–5, 1975), and AKITA mice (Yoshioka M., et al., Diabetes 46, 887–894, 1997).

Of these animals, KK-Ay mice and NSY mice are models with obesity and db/db mice and ob/ob mice are models with obesity due to an abnormality in leptin receptors or in leptin production. On the other hand, AKITA mice are a model for diabetes caused by an abnormality in pancreatic β cells.

On the other hand, most of diabetes patients in Japan, of which more than 90% are Type II diabetes patients, are known to be nonobese Type II diabetes patients without obesity. Therefore, the development of model animals for Type II diabetes without obesity has been desired since conventional Type II diabetes model animals are not satisfactory to elucidate the cause of nonobese Type II diabetes and to establish a method for the treatment thereof.

As a nonobese Type II diabetes model animal, for example, a model mouse is so far reported in Japanese Patent Laid-Open Publication No. 2004-65181. This mouse exhibits abnormal insulin secretion.

The onset and symptoms of Type II diabetes are known to be closely associated with two factors, a decrease in insulin secretion and a decrease in insulin sensitivity (insulin resistance).

SUMMARY OF THE INVENTION

The present inventors recently succeeded in generating a mouse in which Type II diabetes was developed spontaneously. This mouse essentially had no obese tendency. Further, this mouse had normal pancreatic β cells and exhibited normal insulin secretion. These characteristics were different from those of conventional Type II diabetes model mice. The present invention has been made based on these findings.

Accordingly, an objective of the present invention is to provide a novel mouse having a gene which develops spontaneous Type II diabetes.

Further, a Type II diabetes model mouse according to the present invention is characterized in that it comprises a causative gene which can express the following characteristics (1) to (3) in the heterologous or homologous state and the abovementioned characteristics are autosomal recessive genetic traits:

(1) having a higher blood sugar level hyperglycemic as compared to a normal strain mouse at 10 to 14 weeks of age and having a blood glycosylated hemoglobin ($HbA_{1c}$) concentration of 2.5% or higher at 10 to 14 weeks of age or older, (2) exhibiting positive in test for urine sugar at 10 to 14 weeks of age, and (3) being essentially no inflammation of the pancreatic islets and having a blood insulin concentration equivalent to or higher than that of a normal strain mouse.

According to one preferred embodiment of the present invention, the abovementioned causative gene can further express the following characteristic:

(4) exhibiting essentially no obese tendency.

According to another embodiment of the present invention, there is provided a congenic mouse which is a progeny of the mouse according to the present invention having the characteristics (1) to (4), and can be obtained by introducing the causative gene into any laboratory mouse through backcrossing.

According to further another embodiment of the present invention, there is provided an embryo of a Type II diabetes model mouse according to the present invention.

Further, a method for generating the congenic mouse according to the present invention is a method for generating the congenic mouse having the characteristics (1) to (3) comprising backcrossing by using a Type II diabetes model mouse, which is characterized in that it has a causative gene which can express the characteristics (1) to (3) in the homologous state, the characteristics being autosomal recessive genetic traits, as a donor parent, and using any laboratory mouse as a recurrent parent.

DETAILED DESCRIPTION OF THE INVENTION

Deposition of Embryo

Figure 1:
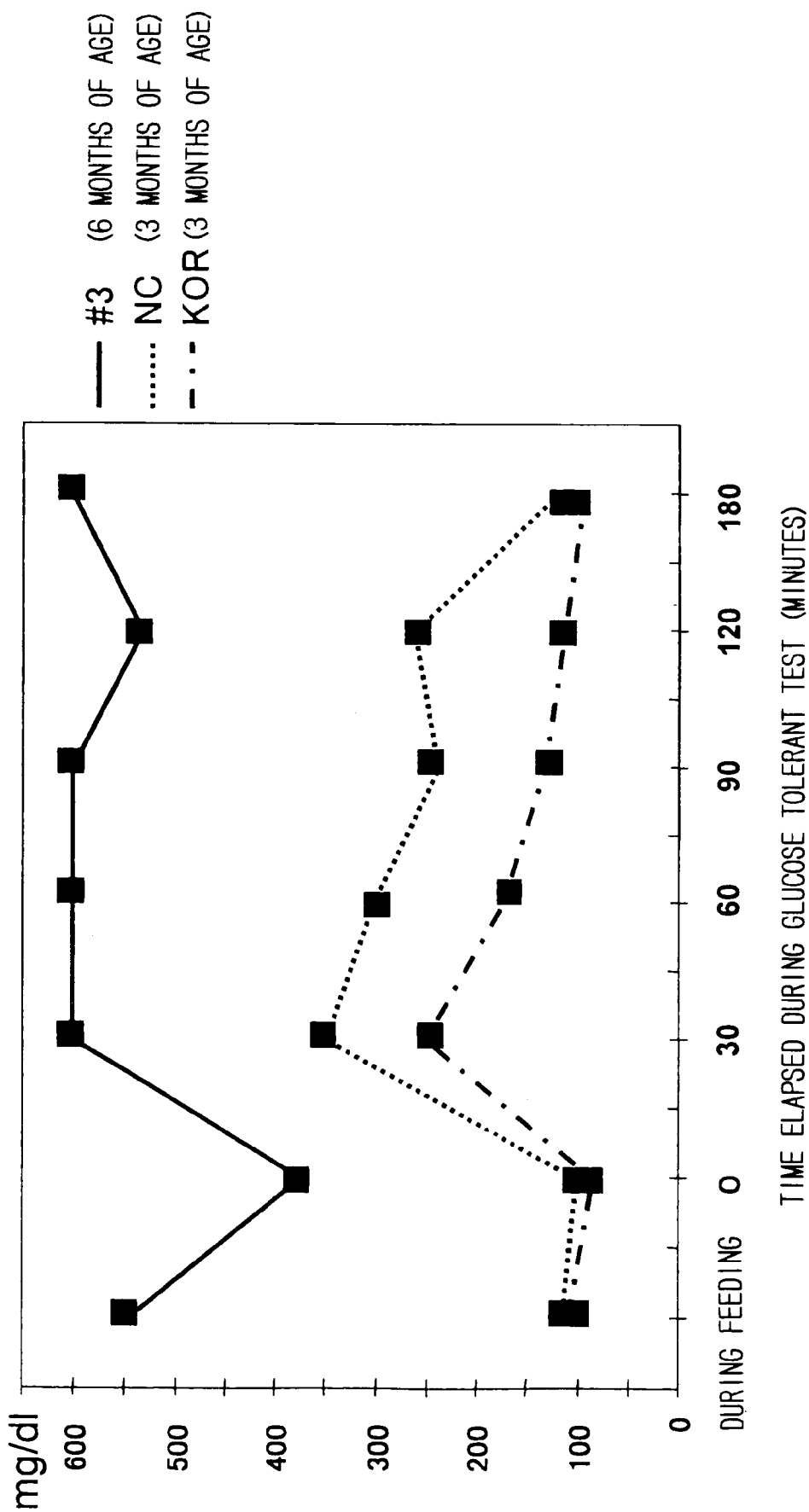
FIG. 1 shows the results of the glucose tolerance test in Examples.

An embryo (a fertilized egg) of a mouse according to the present invention, namely an embryo of a mouse which has a causative gene responsible for the abovementioned characteristics (1) to (3) in the heterologous state was deposited to International Patent Organism Depositary, National Institute of Advanced Industry and Technology, Central 6, 1-1-1 Higashi, Tsukuba, Ibaraki, 305-8566, Japan, dated as of Jul. 21, 2004 (original deposition date) under the name "Type II diabetes mouse" with an Accession Number of FERM BP-10202.

The Mouse According to the Present Invention

In this specification, the term "Type II diabetes model mouse" means a mouse which has a causative gene for the abovementioned characteristics (1) to (3) of the Type II diabetes model mouse in the homologous or heterologous state as the gene type, unless otherwise stated. Accordingly, as for a Type II diabetes model mouse according to the present invention, the kind of mouse (strain, hybrid, etc.), namely the kind of mouse itself as a genetic background, is not particularly limited as long as the mouse has the causative gene for the abovementioned characteristics in the heterologous or homologous state. Examples of the strain of such a mouse thus include an inbred KOR mouse strain and atopic dermatitis model NC mouse strain from which a Type II diabetes model mouse according to the present invention was derived, as well as a C3H/He mouse strain, BALB/c mouse strain, C57BL/6 mouse strain, AKR/Ms mouse strain, and A/J mouse strain.

In the present specification, "homozygote" means a mouse which has a causative gene responsible for the abovementioned characteristics (1) to (3) in the homologous state and "heterozygote" means a mouse which has said causative gene in the heterologous state.

Accordingly, the Type II diabetes model mouse according to the present invention implies both a homozygote which spontaneously develops Type II diabetes and a heterozygote which does not develop Type II diabetes. Further, a heterozygote may be advantageous in generating, transporting and the like since it has a life span equivalent to that of a normal mouse and is thus easy to handle.

In one preferred embodiment of the present invention, a Type II diabetes model mouse has its causative gene in the homologous state. In another preferred embodiment of the present invention, a Type II diabetes model mouse has its causative gene in the heterologous state.

In the present specification, the term "spontaneous development" means that Type II diabetes can be developed by inheriting naturally derived traits such as mutations or that Type II diabetes can potentially be developed. The expression "Type II diabetes can potentially be developed" means as used herein that the causative gene is present in the heterologous state. Accordingly, a mouse of the present invention either spontaneously develops Type II diabetes or has a potential to spontaneously develop Type II diabetes and is distinctly different from mice in which genes are artificially manipulated using genetic engineering technology, such as knockout type mice and transgenic type mice.

Origin of the Mouse

The present inventors found a mouse which spontaneously develop Type II diabetes among F2 generation mice, which were generated by crossing an inbred KOR mouse derived from mice of Japanese wild-type strain (*Mus musculus molossinus*) trapped in Koriyama, Fukushima, Japan in 1988 and 1989 and an NC mouse that is an atopic dermatitis model mouse (NC/Jic mouse available from Clea Japan, Inc.).

Accordingly, the Type II diabetes model mouse according to the present invention is typically progeny between the inbred KOR mouse and the atopic dermatitis model NC mouse.

Characteristics of the Mouse

The Type II diabetes model mouse according to the present invention has a causative gene which expresses the following characteristics 1) to 5) in the heterologous or homologous state.

1) Physiological Characteristics

The Type II diabetes model mouse according to the present invention (homozygote) has the following physiological characteristics, typically at least the following characteristics (i) to (iv).

(i) Blood Sugar:

The Type II diabetes mouse model according to the present invention (homozygote) has a higher blood sugar level at 10 to 14 weeks of age as compared to a normal strain mouse.

The "normal strain mouse" herein is not particularly limited and can be any mouse as long as it shows no abnormality in the blood sugar level, urea sugar, insulin secretion and the like. Preferred examples of the "normal strain mouse" include a KOR mouse, NC mouse, and laboratory mouse which is used as a recurrent parent in generating a congenic mouse (e.g., C3H/He mouse, BALB/c mouse, and C57BL/6 mouse).

The expression "having a higher blood sugar level as compared to a normal strain mouse" means that the blood sugar level (glucose concentration in the blood) at fasting is higher than that of a normal strain mouse at fasting, preferably 130 mg/dl or higher, more preferably 140 mg/dl or higher, further preferably 200 mg/dl and further more preferably 300 mg/dl or higher. Further, the term "fasting" as used herein means a condition about 12 hours after the start of fasting of a mouse.

In the present invention, the "blood sugar level" can be measured by a conventional method, for example, using a commercial measuring apparatus (e.g., Medisafe Reader; Terumo Co., Ltd.) according to the method described in Example hereinafter.

(ii) Glycosylated Hemoglobin ($HbA_{1c}$) Concentration:

The Type II diabetes model mouse according to the present invention (homozygote) shows a blood glycosylated hemoglobin concentration of 2.5% or higher, more preferably 2.6% or higher, further preferably 2.8% or higher, and further more preferably 3.0% or higher, at 10 to 14 weeks of age or older.

The "glycosylated hemoglobin concentration" as used herein means the proportion of hemoglobin molecules with glucose attached to them in a red blood cell. The glycosylated hemoglobin concentration can be used as an index to judge appropriateness of therapeutic control for diabetes patients and is known to correlate better with the blood sugar level at 1 to 2 months earlier than with that at the present time.

The "glycosylated hemoglobin concentration" can be measured by a conventional method, for example, using a commercial measuring apparatus (e.g., DCA 2000 System; Bayer Medical Ltd.) according to the method described in Example hereinafter. More specifically, for example, when the abovementioned DCA 2000 System is used as a measuring apparatus, the amount of total hemoglobin is measured by the thiocyan-methemoglobin method and the amount of glycosylated hemoglobin is measured by the latex coagulation inhibition reaction.

(iii) Urine Sugar:

The Type II diabetes model mouse according to the present invention (homozygote) indicates positive in test for urine sugar at 10 to 14 weeks of age.

The term "positive in test for urine sugar" as used herein means that the glucose concentration in the urine excreted by the mouse is 100 mg/dl or higher. The urine glucose concentration can be measured by a conventional method, for example, by the method described in Example hereinafter using a commercial kit (e.g., Pretest; Wako Pure Chemical Industries, Ltd.). Specifically, for example, when the Pretest is used as a measuring kit, a mouse urine sample is first put on a test paper of the Pretest, and after 30 seconds a judgment is made according to the specified color table in this kit for the classification into five grades ranging from – to +4. Urine glucose concentrations estimated from the result of the judgment are 100–250 mg/dl for +1, 250–500 mg/dl for +2, 500–2000 mg/dl for +3, and 2000 mg/dl or higher for +4. The judging results of +1 and higher are assessed as "positive in test for urine sugar."

(iv) Blood Insulin Concentration:

The blood insulin concentration of the Type II diabetes model mouse according to the present invention (homozygote) is equivalent to or higher than that of a normal strain mouse.

The expression that the blood insulin concentration is "equivalent to or higher than that of a normal strain mouse" means that the blood insulin concentration at fasting is equivalent to or higher than that of a normal strain mouse at fasting, preferably 90 pg/ml or higher, more preferably 110 pg/ml or higher.

In the present invention, the "blood insulin concentration" can be measured by a conventional method, for example, using a Levis insulin assay kit U-type (Shibayagi Co.) according to the method described in Example hereinafter. More specifically, for example, an anti-insulin monoclonal antibody (mouse) is immobilized onto a plate, insulin in a sample is bound thereto, after which a biotin-labeled anti-insulin monoclonal antibody which recognizes another site of insulin is reacted therewith, a peroxidase-avidin conjugate is further added thereto to bind to biotin, and finally a chromogenic substance is added to measure insulin by color development.

(v) Glucose Tolerance:

The Type II diabetes model mouse according to the present invention (homozygote) shows abnormal glucose tolerance.

Whether the glucose tolerance of a mouse is normal or abnormal can be confirmed by a glucose tolerance test. The glucose tolerance test can be carried out according to a conventional procedure, for example, by intraperitoneally administering glucose to a fasting mouse at 1 mg per gram of bodyweight and measuring the blood glucose level of the mouse at certain times during the glucose tolerance test (for example, every 30 minutes over 180 minutes). When the result shows that the blood glucose level shows no tendency to decrease with time as compared with that for a normal mouse, the glucose tolerance is assessed as abnormal.

(vi) Others:

The Type II diabetes model mouse according to the present invention (homozygote) shows tendencies of increased water drinking and increased urination, after the onset of diabetes, typically after 10 to 14 weeks of age. The tendency of increased water drinking can be confirmed, for example, by carefully monitoring the rate of decrease in the water volume in a water bottle placed in a rearing cage and comparing it with that for a normal strain mouse. Further, the tendency of increased urination can be confirmed, for example, by observing the extent of wetting of a floor sheet in the rearing cage and comparing it with that for a normal strain mouse.

2) Histopathological Characteristics

No inflammation is substantially detected in pancreatic islets (Langerhans islets) of the Type II diabetes model mouse according to the present invention (homozygote).

The expression "no inflammation is substantially detected in pancreatic islets" means that no damage or destruction of pancreatic islet β cells, except minor changes such as partial atrophy of pancreatic islet β cells, was detected when a pathological examination is performed. The pathological examination herein can be performed by the method described in Example hereinafter.

In the mouse according to the present invention, insulin secretion is deemed normal since no pancreatic islet inflammation is substantially detected. The normality in insulin secretion can be confirmed by measuring the blood insulin concentration and comparing it with that for a normal strain mouse as mentioned above.

3) Obesity

No obese tendency is substantially detected in the Type II diabetes model mouse according to the present invention (homozygote).

The presence or absence of obese tendency can be judged by comparing the bodyweight of the mouse with that of a normal strain mouse at the same weeks of age. Upon judging, statistical measures (such as a significance test) can be applied using multiple samples.

4) Mode of Inheritance

The characteristics of the Type II diabetes model mouse according to the present invention are traits controlled by an autosomal recessive gene. Namely, a crossing experiment using the mouse according to the present invention showed that Type II diabetes was developed by the mode of autosomal recessive inheritance, following simple Mendelian inheritance laws. The Type II diabetes of the mouse according to the present invention is developed when its causative gene is present in the homologous state (homozygote). On the other hand, diabetes-related indices, such as the blood glucose level, glycosylated hemoglobin concentration and urine glucose, are normal in a heterozygote.

Therefore, F1 individuals obtained by the cross between the Type II diabetes model mouse according to the present invention (homozygote) and a laboratory mouse exhibit no pathological change since they are heterozygotes. F2 individuals obtained by the cross between two of the F1 individuals develop Type II diabetes since about ¼ of F2 become homozygotic.

5) Difference in Frequency of Diabetes Development Between the Sexes

In the Type II diabetes model mouse according to the present invention, there is little difference in the frequency of diabetes development between the sexes.

Namely, it is said that there is no difference between the sexes in the frequency of development of both Type I and Type II diabetes in Japan. However, it has been reported that in Type II diabetes model KK mice, about 80% of males are positive in test for urine sugar at 17 to 18 weeks of age even when fed general feed while females are less obese and less diabetic than males (Nishimura, M., Exp. Anim. 18:147–157, 1969). Further, it has been reported that in Type II diabetes model Akita mice, there is also some difference between the sexes in diabetes development; males develop diabetes more severely than females and their one-year survival rate is as low as 50% while the survival rate for females is almost 100%, as high as that for normal counterparts (Yoshioka, M., et al., Diabetes 46:887–894, 1997).

It has also been reported that in NYS (Nagoya Shibata Yasuda) mice, another Type II diabetes model, which develop diabetes after 8 weeks of age, the accumulative incidence rate up to 48 weeks of age is almost 100% for males and about 20% for females (Ueda, H., et al., Diabetologia 38:503–508, 1995). Thus, for these mouse strains, the difference in diabetes development is recognized between the sexes and the incidence is more frequent and the symptoms are more severe in males than in females. On the other hand, also in type I diabetes model NOD mice, the difference in the incidence rate has been recognized between the sexes. It has been reported that in contrary to the cases for the abovementioned model mice such as the KK mice, the incidence rate is higher in females; namely the accumulative rate up to 30 weeks of age is 90% for females and 50% for males (Hattori, M., et al., Science 231:733–742, 1986).

In contrast to these mice, the Type II diabetes mice according to the present invention so far show no substantial difference between the sexes in the incidence rate, although they are still in the process of strain establishment. Accordingly, both sexes of the mice according to the present invention can be used for a model animal experiment and the animals can be obtained in sufficient numbers. Further, no difference in the incidence is observed between the sexes similarly to the case of human diabetes, which makes them an excellent model.

Generation of Mice

Reproductivity of male mice of the Type II diabetes mouse strain according to the present invention (homozygotes) tends to decline with aging. Accordingly, it is desirable to rear homozygous males and females together at early breeding age for the maintenance of the strain. Alternatively, the strain can be maintained by crossing heterozygous female individuals with homozygous male individuals. Of the progenies obtained by such crossings, both female and male individuals which develop Type II diabetes are all homozygous while both female and male normal individuals are heterozygous.

When the second generation is further needed, it can similarly be obtained, for example, by crossing heterozygous female individuals and homozygous male individuals.

The homozygotes and the heterozygotes can be easily distinguished by measuring their blood glucose level and urine sugar at 8 to 10 weeks of age. Ultimately, they can be distinguished more precisely by judging from the measurement of their glycosylated hemoglobin level at 10 to 14 weeks of age.

Breeding of Mice

The necessary number of mice can be bred by brother-sister mating as ordinarily done in the breeding of inbred animals.

For example, a heterozygous female individual is crossed with a homozygous male individual and a large number of individuals of interest can be obtained by selecting homozygous individuals from the generated offspring using the abovementioned distinguishing measure.

Therefore, according to another embodiment of the present invention, there is provided a method of generating a spontaneous Type II diabetes model mouse by crossing the Type II diabetes model mice according to the present invention among themselves and selecting a mouse having a causative gene responsible for diabetes developing characteristics in the homologous state.

Rearing Conditions for Mice

Rearing conditions for Type II diabetes model mice according to the present invention are not particularly limited and the mice can be reared according to an ordinary rearing method. For example, they can be reared under SPF conditions at room temperature, i.e., at 22±2° C. and at a humidity of 65±5%, continuously fed a normal feed (for example, F2; Funabashi Farm, Inc.) and given tap water ad libitum. Further, the mice can be reared in an aluminum cage spread with wood chips on the floor.

The mice according to the present invention include hybridized mice obtained by crossing with a laboratory mouse and congenic mice described hereinafter.

Congenic Strain Mouse

According to the present invention, there is provided a congenic Type II diabetes model mouse, which is obtained by introducing a causative gene expressing the characteristics (1) to (3) into any laboratory mouse through backcrossing, namely a congenic mouse. This congenic mouse has a genetic background of the laboratory mouse, except for the abovementioned causative gene. This congenic mouse also develops Type II diabetes because it has the abovementioned causative gene.

Such a congenic mouse can be generated by backcrossing a Type II diabetes model mouse according to the present invention (homozygote) with any laboratory mouse using a known backcross breeding method. In such a case, the Type II diabetes model mouse according to the present invention (homozygote) is used as a donor parent and the laboratory mouse is used as a recurrent parent. Generally, in order to establish congenic mouse strains by backcrossing, at least 8 generations, typically about 12 generations of crossing are required.

Further, examples of the laboratory mouse to be used here include C3H/He mice, BALB/c mice, C57BL/6 mice, NC/Jic mice, AKR/Ms mice, and A/J mice. C3H/He mice, BALB/c mice, and C57BL/6 mice are preferred.

According to another embodiment of the present invention, there is provided a method of generating a congenic mouse which can exhibit the abovementioned characteristics (1) to (3), comprising backcrossing by using a Type II diabetes model mouse having a causative gene which can express the characteristics (1) to (3) in the homologous state, said characteristics being autosomal recessive genetic traits, as a donor parent, and using any laboratory mouse as a recurrent parent. Here, the Type II diabetes model mouse to be used is preferably a homozygous mouse induced from the mouse whose embryo has been deposited with the abovementioned accession number.

In one embodiment, the present inventors generated 3 lineages of congenic mice having different genetic backgrounds, in which laboratory mice used are a C57BL/6 mouse and a BALB/c mouse which exhibit poor glucose tolerance and a C3H/He mouse which exhibits excellent glucose tolerance.

For example, as described in Example hereinafter, the present inventors confirmed that there is phenotypic difference in all the mice of the BALB/c strain, C57BL/6 strain and C3H/He strain during the generating process when compared to that in normal strain mice. Under these circumstances, anyone skilled in the art will be able to understand that the generation of congenic mice is possible.

The congenic mouse with a causative gene introduced into a laboratory mouse has a genetic background different from that of the Type II diabetes model mouse according to the present invention which is the donor parent as mentioned above. Therefore, the Type II diabetes model mouse according to the present invention, i.e., the donor parent, and the congenic mouse are useful in analyzing the effect of the difference in genetic backgrounds on the pathological conditions of Type II diabetes.

Usefulness as an Animal Model (a) The Type II diabetes model mouse according to the present invention (homozygote) exhibits no abnormality in insulin secretion caused by abnormal pancreatic β cells. Further, the mouse according to the present invention shows almost no obese tendency. Conventionally, known non-obese model mice for Type II diabetes exhibit abnormal insulin excretion. Therefore, the model mouse according to the present invention can be a strain of a novel model mouse in regard to Type II diabetes and thus is considered to be a useful model mouse for research on the mechanism of development of Type II diabetes and its treatment and prevention and in the field of pharmaceutical medicine.

(b) By using the Type II diabetes model mouse according to the present invention, a congenic strain thereof can be generated. The generation of such a congenic mouse is considered to be useful in elucidating the mechanism of development of Type II diabetes, which is still largely unclear, searching for new therapeutic strategies and pharmaceuticals, developing order-made therapy, and establishing preventive measures. Further, the laboratory mouse used for the genetic background in generating the congenic mouse can be used as a normal control mouse for comparison. Further, by making the mouse congenic, its reproductivity can be improved and its life span can be prolonged. In addition, in the present invention, a diabetes mouse according to the present invention is subjected to backcrossing individually with mice of 3 inbred strains (C3H/He, C57BL/6 and BALB/c mice) to generate respective congenic mice. Glucose tolerance is known to be different between different strains of the inbred mice and C3H/He mice is known to have higher glucose tolerance than C57BL/6 and BALB/c mice. Thus, according to the present invention, multiple strains of model mice having difference in glucose tolerance between the strains can be established, which makes it possible to elucidate the interaction between genetic factors and environment factors involved in the mechanism of diabetes development, thus generating an epoch-making series of disease models.

EXAMPLE

The present invention is further illustrated by the following examples that are not intended as a limitation of the invention.

Process of Generation

The Type II diabetes model mouse of the present invention was found in 2003 among F2 generation mice which were generated by crossing between an inbred KOR mouse derived from mice of a Japanese wild-type strain (*Mus musculus molossinus*) trapped in Koriyamashi, Fukushima Prefecture, Japan and a commercial NC mouse which is an atopic dermatitis model mouse (NC/Jic mouse available from Clea Japan, Inc.). Abnormal wetting and soiling were found on a floor sheet in a cage where the abovementioned F2 generation mouse were housed, and it was found by observation that these abnormal wetting and soiling were caused by excessive urination. Further, excessive drinking was confirmed by observing the rate of water decrease in a water bottle, from which the development of diabetes was suspected. Results of testing the blood glucose level and urine sugar of the abovementioned F2 generation mouse showed that the mouse was hyperglycemic and positive in test for urine sugar. In this way, the mouse which spontaneously developed Type II diabetes was found.

This mouse was further studied and at the same time, assuming that this abnormality was a genetic disorder, Type II diabetes mice were isolated and generated through crossing experiments between parent/offspring and brother/sister to obtain the mouse according to the present invention.

Namely, the strain of the Type II diabetes model mouse according to the present invention was a mutant strain found among the crossbreeds between its KOR strain and a commercially available NC strain and thus established as a mutant strain Type II diabetes model mouse. Further, the KOR strain mouse, which makes the firstly found background moiety, have already been inbred for more than 24 generations (F24).

The Type II diabetes model mice according to the present invention were reared under SPF conditions at room temperature, i.e., at 22±2° C. and at a humidity of 65±5%. They were continuously fed a normal feed (F2; Funabashi Farm, Inc.). They were given tap water from water bottles ad libitum and reared in an aluminum cage spread with wood chips on the floor.

Measurement of Blood Sugar Level

The blood sugar level (blood glucose concentration) of a subject mouse was measured using a commercial measuring apparatus (Medisafe Reader, Terumo Co., Ltd.). Measurement principle of this apparatus will be explained as follows. The measurement is based on calorimetric analysis. A measuring chip is prepared, and onto the chip are placed glucose oxidase and peroxidase as catalysts and 4-aminoantipyrine and N-ethyl-N(2-hydroxy-3-sulfopropyl)-m-toluidine as chromogenic agents. When a blood sample absorbed through capillary phenomenon is placed on this chip and then glucose in the blood is oxidized by glucose oxidase. Then, the chromogenic agents on the chip are oxidized by hydrogen peroxide generated at this moment and peroxidase, which yields a red-purple color. The amount of glucose in the blood is calculated by measuring the degree of this color tone.

Here, 4 μl of the whole blood was obtained from a subject mouse as a blood sample and measured using a measurement time of 18 seconds.

Sample #1 and sample #3 were selected as Type II diabetes strain mice according to the present invention (homozygotes) and their blood sugar level was measured. The blood sugar level of a normal strain mouse, C57BL/6 mouse, was also measured for comparison.

The results are shown in Table 1.

TABLE 1

| Sample | Blood sugar level (mg/dl) | Urine sugar | Blood insulin conc. (pg/ml) |
| --- | --- | --- | --- |
| # 1 | 529 | +4 | 40 |
| # 3 | 470 | +4 | 90 |
| Comparative example | 100–110 | — | 110 |

Measurement of Urine Sugar

The urine glucose (urine sugar) of a subject mouse was measured using a commercial kit (Pretest; Wako Pure Chemical Industries, Ltd.). First, a mouse urine sample was blotted into a test paper of the abovementioned Pretest, and after 30 seconds judgment was made according to a color table specified for the classification into five grades ranging from − to +4. Urine glucose concentrations estimated from the results of the judgment are 100–250 mg/dl for +1, 250–500 mg/dl for +2, 500–2000 mg/dl for +3, and 2000 mg/dl or higher for +4. The judging results of +1 and higher were assessed as "positive in test for urine sugar."

Sample #1 and sample #3 were selected as Type II diabetes strain mice according to the present invention (homozygotes) and their urine sugar was measured. The urine sugar of a normal strain mouse, C57BL/6 mouse, was also measured for comparison.

The results are shown in Table 1.

Measurement of Blood Insulin Concentration

The blood insulin concentration of a subject mouse was measured using a commercial kit (Levis insulin assay kit U-type; Shibayagi Co.). The insulin concentration was measured in the following manner. An anti-insulin monoclonal antibody (mouse) was immobilized onto a plate, insulin in a sample was bound to it, after which a biotin-labeled anti-insulin monoclonal antibody, which recognizes another portion of insulin, was reacted, a peroxidase-avidin conjugate was further added thereto to bind to biotin, and finally a chromogenic substance was added to measure insulin by color development. The range of measurement is generally from 39 to 2,500 pg/ml for a normal mouse.

Sample #1 and sample #3 were selected as Type II diabetes strain mice according to the present invention (homozygotes) and their blood insulin concentration was measured. The blood insulin concentration of a normal strain mouse, C57BL/6 mouse, was also measured for comparison.

The results are shown in Table 1.

Evaluation of Glucose Tolerance

The glucose tolerance of a subject mouse was evaluated by the following glucose tolerance test.

The glucose tolerance test was carried out by first administering glucose intraperitoneally to a 24-hour fasting mouse at 1 mg per gram of bodyweight and then measuring the glucose level in the blood (peripheral blood) of the mouse every 30 minutes over 180 minutes. The blood glucose level was measured by the abovementioned method. When the result showed that the blood glucose level exhibited no tendency to decrease with time as compared with that for a normal mouse, the glucose tolerance was assessed as abnormal.

Sample #3 (6 months of age) were selected as a Type II diabetes model mouse according to the present invention (homozygote), normal strain mice, a KOR mouse (3 months of age) and an NC mouse (3 months of age), were selected as comparative examples and they were subjected to the glucose tolerance test.

The results are shown in FIG. 1.

Histopathological Examination

The pancreatic tissue of a Type II diabetes mouse according to the present invention (homozygote) and the pancreatic tissue of a normal mouse (KOR mouse) were fixed with 10% formalin, then embedded in paraffin, stained with hematoxylin-eosin (H-E) by an ordinary method, and then observed under a microscope (at 400× magnification).

The results showed that in the mouse according to the present invention, no damage or destruction of pancreatic islet (Langerhans islet) β cells was observed although partial atrophy of the pancreatic tissue, in particular in pancreatic islet β cells, was observed when compared to the normal mouse.

Judgment of the Presence or Absence of Obese Tendency in Mice

Among the F2 mice on the process of the congenic mouse generation, the body weights of mice (homozygotes) with symptoms developed and mice without symptoms (heterozygotes and normal homozygotes) were measured and compared.

When the body weights of males of C57BL/6 strain were compared, mice with symptoms weighed 35.6±8.3 g (n=28; n is the number of individuals measured) and mice without symptoms weighed 36.7±9.7 g (n=42). Thus, there was no significant difference in the body weight between the mice with symptoms (homozygotes) and the mice without symptoms.

Generation of Congenic Mice

Congenic mouse strains were generated by backcrossing a Type II diabetes model mouse according to the present invention (homozygote) and a laboratory mouse by a known backcrossing breeding method. In the backcrossing, the Type II diabetes model mouse (homozygote) was used as a donor parent and the laboratory mouse was used as a recurrent parent.

As laboratory mice, a C57BL/6 mouse and BALB/c mouse having poor glucose tolerance and a C3H/He mouse having excellent glucose tolerance were used. In this way, three congenic strains of mice each having a different genetic background were generated.

The blood sugar level and the glycosylated hemoglobin concentration were measured for the three different strains of the crossed mice (F2 individuals with symptoms), i.e., BALB/c strain, C57BL/6 strain, and C3H/He strain, obtained in the process of establishing the congenic mouse strains. The blood sugar level was measured according to the abovementioned measuring method.

The glycosylated hemoglobin concentration was measured using a commercial measuring apparatus (DCA 2000 System; Bayer Medical Ltd.). The principle of the measurement was that the amount of total hemoglobin was measured by the thiocyan-methemoglobin method and the amount of glycosylated hemoglobin was measured by the latex coagulation inhibition reaction. Here, the measurement ranged from 2.5% to 14.0%, and the concentration less than 2.5% was represented by <2.5%. First, a capillary was filled with 1 μl of a whole blood sample for detection and attached to the apparatus main body. The time of the measurement was 6 minutes.

Further, the measurement was also carried out for a normal strain mouse, C57BL/6 mouse, for comparison.

The results are shown in Table 2.

TABLE 2

| Genetic background strain of mouse obtained in congenic mouse establishing process | Blood sugar level(mg/dl) | SD | HbA$_{1c}$ (%) | SD |
|---|---|---|---|---|
| C3H/He (n = 8) | 146.5 | 44.9 | 2.5 | 0.1 |
| C57BL/6 (n = 16) | 151.3 | 31.2 | 3.0 | 0.2 |
| BALB/c (n = 7) | 143.6 | 23.7 | 3.1 | 0.4 |
| Comparative example* (n = 9) | 105 | 19.3 | <2.5 | 0.1 |

*C57BL/6

In the Table, SD is standard deviation, n is the number of individuals used for the measurement, and the blood sugar level and the glycosylated hemoglobin concentration are averages of the measurements for the individuals.

As evident from the Table, as for the glycosylated hemoglobin concentration, a significant difference presumably due to the difference in genetic background was recognized.

What is claimed is:

1. A Type II diabetes mouse model, comprising a mouse grown from an embryo deposited under the Budapest Treaty with an accession number of FERM BP-10202 which exhibits the following characteristics (1) to (3), wherein said characteristics are autosomal recessive genetic traits:
   (1) having a higher blood sugar level as compared to a normal strain mouse at 10 to 14 weeks of age and having a blood glycosylated hemoglobin ($HbA_{1c}$) concentration of 2.5% or higher at 10 to 14 weeks of age or older,
   (2) being positive in test for urine sugar at 10 to 14 weeks of age, and
   (3) exhibiting no inflammation of the pancreatic islets and having a blood insulin concentration equivalent to or higher than that of a normal strain mouse.

2. The mouse model according to claim 1, which further exhibits the following characteristic:
   (4) exhibiting no obese tendency.

3. A mouse which is progeny of the mouse model of claim 1 and can exhibit the characteristics listed in claim 1.

4. The mouse model according to claim 3, which is a congenic mouse obtained by backcrossing a mouse grown from an embryo deposited under the Budapest Treaty with an accession number of FERM BP-10202 which exhibits said characteristics (1) to (3) with any laboratory mouse.

5. A method of generating a congenic mouse which exhibits the following characteristics:
   (1) having a higher blood sugar level as compared to a normal strain mouse at 10 to 14 weeks of age and having a blood glycosylated hemoglobin ($HbA_{1c}$) concentration of 2.5% or more at 10 to 14 weeks of age or older,
   (2) being positive in test for urine sugar at 10 to 14 weeks of age, and
   (3) exhibiting no inflammation of the pancreatic islets and having a blood insulin concentration equivalent to or higher than that of a normal strain mouse, comprising backcrossing by using a Type II diabetes mouse model grown from an embryo deposited under the Budapest Treaty with an accession number of FERM BP-10202 which exhibits the characteristics (1) to (3), said characteristics being autosomal recessive genetic traits, as a donor parent, and using any laboratory mouse as a recurrent parent.

6. The method according to claim 5, wherein said congenic mouse further exhibits the following characteristic: (4) exhibiting no obese tendency.

* * * * *

UNITED STATES PATENT AND TRADEMARK OFFICE
CERTIFICATE OF CORRECTION

PATENT NO. : 7,202,393 B2 Page 1 of 1
APPLICATION NO. : 11/041013
DATED : April 10, 2007
INVENTOR(S) : Matsushima It is certified that error appears in the above-identified patent and that said Letters Patent is hereby corrected as shown below:

Title Page;
Face of the Patent, See Item (56) References Cited, FOREIGN PATENT DOCUMENTS,
 " JP  20040651581   3/2004" should read
-- JP  2004065181    3/2004 --

Signed and Sealed this

Fourteenth Day of August, 2007

JON W. DUDAS
*Director of the United States Patent and Trademark Office*